United States Patent [19]

Klotz

[11] 4,390,457
[45] Jun. 28, 1983

[54] SYNTHESIS OF MOLECULAR SIEVES USING 2-AMINOPYRIDINE AS A TEMPLATE

[75] Inventor: Marvin R. Klotz, Batavia, Ill.

[73] Assignee: Standard Oil Company (Indiana), Chicago, Ill.

[21] Appl. No.: 305,976

[22] Filed: Sep. 28, 1981

[51] Int. Cl.$^3$ .................. C01B 33/28; B01J 29/06
[52] U.S. Cl. .................. 252/455 Z; 423/328; 423/329
[58] Field of Search .................. 423/326–330; 252/431 N, 455 Z; 546/2, 14

[56] References Cited

U.S. PATENT DOCUMENTS

| | | | |
|---|---|---|---|
| 3,459,676 | 8/1969 | Kerr | 423/329 |
| 4,000,248 | 12/1976 | Martin | 423/329 |
| 4,205,052 | 5/1980 | Rollmann | 423/328 |
| 4,205,053 | 5/1980 | Rollmann et al. | 423/329 |
| 4,251,499 | 2/1981 | Nanne et al. | 423/329 |
| 4,285,922 | 8/1981 | Audeh et al. | 423/328 |

*Primary Examiner*—Edward J. Meros
*Attorney, Agent, or Firm*—Wallace L. Oliver; William T. McClain; William H. Magidson

[57] ABSTRACT

Crystalline aluminosilicate molecular sieves are formed by (1) forming an aqueous mixture of an oxide of aluminum, an oxide of silicon, a metal or ammonium cation and 2-aminopyridine organic template compound, (2) maintaining the pH of such mixture between about 9 and 13.5, and (3) crystallizing the mixture.

25 Claims, No Drawings

SYNTHESIS OF MOLECULAR SIEVES USING 2-AMINOPYRIDINE AS A TEMPLATE

BACKGROUND OF THE INVENTION

This invention relates to a new method of preparing crystalline aluminosilicate molecular sieve compositions with advantageous properties.

Zeolitic materials, both natural and synthetic, are known to have catalytic capabilities for many hydrocarbon processes. Zeolitic materials, typically, are ordered porous crystalline aluminosilicates having a definite structure with cavities interconnected by channels. The cavities and channels throughout the crystalline material generally are uniform in size allowing selective separation of hydrocarbons. Consequently, these materials in many instances are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic positive-ion-containing crystalline zeolite materials. They generally are characterized as crystalline aluminosilicates which comprise networks of $SiO_4$ and $AlO_4$ tetrahedra in which silicon and aluminum atoms are cross-linked by sharing of oxygen atoms. The negative framework charge resulting from the substitution of an aluminum atom for a silicon atom is balanced by the use of, for example, alkali-metal or alkaline-earth-metal cations, ammonium ions, or hydrogen ions.

Prior art developments have resulted in formation of many synthetic zeolitic crystalline materials. Crystalline aluminosilicates are the most prevalent and, as described in the patent literature and in the published journals, are designated by letters or other convenient symbols. Examples of these materials are Zeolite A (U.S. Pat. No. 2,882,243), Zeolite X (U.S. Pat. No. 2,882,244), Zeolite Y (U.S. Pat. No. 3,130,007), Zeolite ZSM-4 (U.S. Pat. No. 3,578,723), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite NU-1 (U.S. Pat. No. 4,060,590) and others.

Shape selective molecular sieves are known in the art. Generally, these sieves are prepared by crystallizing a mixture of sources for an oxide of silicon, an oxide of aluminum, a metal cation, and organic template. Usually, a specific sieve is characterized by a particular range of compositions, such as may be expressed in terms of mole ratios of oxides, coupled with a definite X-ray diffraction pattern. However, it is known that a substance is defined by its properties and that various catalytic substances which ostensibly have similar compositions and X-ray spectra may differ in catalytic properties due to subtle differences around catalytically-active sites. The present invention demonstrates this principle especially in mordenite-like molecular sieves. Such sieves prepared according to this invention possess advantageous properties over other molecular sieves of a similar type having similar compositions and X-ray spectra, but prepared in different manners. It has been discovered that a series of molecular sieves can be prepared using 2-aminopyridine as an organic template. The crystalline forms, as determined from X-ray diffraction analysis, of these compositions include mordenite-like and ferrierite-like forms and forms exhibited in aluminosilicates identified as ZSM-4 and ZSM-5.

Specifically, mordenite compositions described by this invention selectively hydrodealkylate substituted aromatic compounds compared to conventionally-prepared mordenites. Thus, an alkyl substituted aromatic such as ethylbenzene can be converted to benzene or toluene which may have greater value. For example, in a typical feed stream for a xylene isomerization unit contains 5 to 25% of ethylbenzene. A selective catalyst which would hydrodealkylate ethylbenzene to benzene and toluene in xylene isomerization would have substantial utility.

Molecular sieves characterized as "mordenite" by chemical composition and X-ray spectra are known as naturally occurring materials and as synthesized materials. For example, a conventional mordenite sieve is produced by crystallizing a basic mixture of sodium aluminate and an oxide of silicon without the use of an organic template compound. Such mordenites are described in D. W. Breck "Zeolite Molecular Sieves," John Wiley & Sons, 1974, incorporated by reference herein. U.S. Pat. No. 4,061,717 discloses a method of producing a mordenite molecular sieve using an ionene polymer as an organic template compound in the crystallization of the sieve. U.S. Pat. No. 4,107,195 discloses synthetic mordenite prepared as a by-product using 1,4-butanediamine, ethylenediamine and pyrrolidine as organic templates.

Molecular sieves characterized as "ferrierite" by chemical composition and X-ray spectra are known as naturally occurring materials and as synthesized materials. For example, a conventional ferrierite sieve is produced by crystallizing a basic mixture of sodium aluminate and an oxide of silicon without the use of an organic template compound. Such ferrierites are described in D. W. Breck "Zeolite Molecular Sieves," John Wiley & Sons, 1974, incorporated by reference herein. U.S. Pat. No. 4,000,248 discloses a method of producing a ferrierite molecular sieve using N-methyl pyridinium hydroxide as an organic template compound in the crystallization of the sieve. U.S. Pat. Nos. 4,016,245, 4,107,195 and 4,046,859 disclose the formation of a ferrierite-like material using an organic template derived from ethylenediamine, pyrrolidine or butanediamine, or organometallic 2-(hydroxyalkyl)-trialkylaluminum compounds.

Aluminosilicate molecular sieves identified as ZSM-5 are described in U.S. Pat. Nos. 3,702,886 and 4,139,600. Such aluminosilicates are prepared using organic templates such as tetraalkyl ammonium salts, primary alkyl amines and alkylene diamines as described in U.S. Pat. Nos. 4,139,600 and 4,151,189. Aluminosilicate molecular sieve identified as ZSM-4 is described in U.S. Pat. Nos. 3,578,723 and 4,021,447 using organic templates including tetraalkyl ammonium salts, pyrrolidine and choline salts.

SUMMARY OF THE INVENTION

Crystalline aluminosilicate molecular sieves are formed by (1) preparing an aqueous mixture of sources for an oxide of aluminum, an oxide of silicon, a metal or ammonium cation and 2-aminopyridine, (2) maintaining the pH of such mixture between about 9 and 13.5, and (3) crystallizing the mixture.

BRIEF DESCRIPTION OF THE INVENTION

The present invention is a method of producing a molecular sieve using 2-aminopyridine as a template and the product formed therefrom.

Further, this invention is a method of producing a series of crystalline aluminosilicate molecular sieve compositions using identical organic template compounds during crystallization, but yielding crystalline compositions with different X-ray diffraction patterns. By using the 2-aminopyridine organic template compound disclosed in this invention and controlling variables such as the silica/alumina ratios in the crystallization mixture, a series of crystalline aluminosilicate molecular sieves can be produced including aluminosilicates identified as ZSM-4, ZSM-5, mordenite and ferrierite. This invention shows that these aluminosilicates are interrelated in that all can be produced under similar conditions using the same organic template compound but changing the silica/alumina molar ratio in the crystallization mixture. It is observed that as the silica/alumina ratio increases the aluminosilicate usually formed during crystallization of this invention changes in the order: ZSM-5, ferrierite, mordenite, ZSM-4.

The molecular sieve is characterized as a crystalline aluminosilicate having the following chemical composition in terms of oxides:

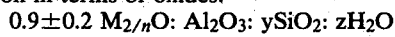

$0.9 \pm 0.2\ M_{2/n}O: Al_2O_3: ySiO_2: zH_2O$ wherein M is at least one cation of valence n, y is between about 2 and about 500, and z is between 0 and about 160, preferably between 0 and 40.

Catalysts prepared using the aluminosilicate of this invention typically are useful to hydrodealkylate alkyl-substituted aromatic compound in which the alkyl groups contain two or more carbon atoms. Conversely, products from disproportionation or transalkylation activity of such catalyst is lowered. The net result of high hydroalkylation activity coupled with low disproportionation/transalkylation activity is a high selectivity for hydrodealkylation. A useful process using the characteristics of the catalyst in a dual component xylene isomerization catalyst system in which a hydrodeethylation catalyst of this invention is used ahead of a conventional xylene isomerization catalyst either in the same reactor or in a separate reactor. The result of such dual catalyst process is to increase ethylbenzene conversion while maintaining low xylene loss.

The molecular sieve of this invention is prepared by crystallizing sources for an aqueous mixture, at a controlled pH, of a source of cations, an oxide of aluminum, an oxide of silicon, and a specific organic template compound.

The method of this invention for preparing crystalline aluminosilicate molecular sieves can form such sieves in different crystalline forms depending on starting materials and reaction conditions. Typically, ferrierite-like material is formed preferentially using silica/alumina molar ratios higher than that employed for mordenite production. Thus, mordenite usually is formed at a $SiO_2/Al_2O_3$ of about 8 while ferrierite usually is formed at a $SiO_2/Al_2O_3$ of about 16.

Other factors which may affect production of a crystalline form include the cation and water concentrations in the crystallization mixture, and the crystallization time and temperature.

By further alteration of the $SiO_2/Al_2O_3$ molar ratio in a crystallization mixture, still different crystalline forms can be made. For example, using lower $SiO_2/Al_2O_3$ molar ratios, an aluminosilicate identified as ZSM-4 can be made having a $SiO_2/Al_2O_3$ molar ratio of about 2 to 30 and typically about 4. At higher $SiO_2/Al_2O_3$ ratios, an aluminosilicate identified as ZSM-5 can be made having X-ray diffraction lines listed in Table IX and $SiO_2/Al_2O_3$ molar ratios of about 4–250 and typically between about 15 and 50.

Generally, in the crystallization mixture of the preparations conducted according to this invention the $OH^-/SiO_2$ molar ratio is between about 0.005 and 10 while the $H_2O/OH^-$ molar ratio is between about 10 and 4000; the $SiO_2/Al_2O_3$ molar ratio can be about 2 to 1000. Further, the $R_2O^+/[R_2O^+ + M_{2/n}O]$ molar ratio is between about 0.1 and 1.0 where R is an organic compound and M is at least one cation having a valence n. Generally, about half of the aluminum present in a crystallization mixture is incorporated into a crystalline aluminosilicate product.

Typically, the mole ratios of the various reactants can be varied to produce the mordenite crystalline aluminosilicates of this invention. Specifically, the mole ratios of the initial reactant concentrations are indicated below:

|  | Broad | Preferred | Most Preferred |
|---|---|---|---|
| $SiO_2/Al_2O_3$ | 2–64 | 4–20 | 8–16 |
| $R_2O^+/[R_2O^+ + M_{2/n}O]$ | 0.1–1.0 | 0.2–0.95 | 0.2–0.95 |
| $OH^-/SiO_2$ | 0.005–10 | 0.01–3 | 0.01–3 |
| $H_2O/OH^-$ | 10–4000 | 10–500 | 10–500 | where R is an organic compound and M is at least one cation having a valence n, such as an alkali metal or an alkaline earth metal cation.

By regulation of the quantity of aluminum (represented as $Al_2O_3$) in the reaction mixture, it is possible to vary the $SiO_2/Al_2O_3$ molar ratio in the final product in a range of from about 2 to about 35 and preferably from about 2 to about 10 and most preferably about 8.

Typically, the mole ratios of the various reactants can be varied to produce the ferrierite crystalline aluminosilicates of this invention. Specifically, the mole ratios of the initial reactant concentrations are indicated below:

|  | Broad | Preferred | Most Preferred |
|---|---|---|---|
| $SiO_2/Al_2O_3$ | 2–128 | 8–40 | 16–32 |
| $R_2O^+/[R_2O^+ + M_{2/n}O]$ | 0.1–1.0 | 0.2–0.95 | 0.2–0.95 |
| $OH^-/SiO_2$ | 0.005–10 | 0.01–3 | 0.01–3 |
| $H_2O/OH^-$ | 10–4000 | 10–500 | 10–500 | where R is an organic compound and M is at least one cation having a valence n, such as an alkali metal or an alkaline earth metal cation.

By regulation of the quantity of aluminum (represented as $Al_2O_3$) in the reaction mixture, it is possible to vary the $SiO_2/Al_2O_3$ molar ratio in the final product in a range of from about 2 to about 65 and preferably from about 4 to about 20 and most preferably about 16.

More specifically, the material of the present invention is prepared by mixing a cation source compound, an aluminum oxide source, and an organic template compound in water (preferably distilled or deionized). The order of addition usually is not critical although a typical procedure is to dissolve sodium hydroxide and sodium aluminate in water and then add the template compound. Generally, after adjusting the pH, the silicon oxide compound is added with intensive mixing such as that performed in a Waring Blendor. After the pH again is checked and adjusted, the resulting slurry is transferred to a stirred, closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of OH-/$SiO_2$ shown above should furnish a pH of the system that broadly falls within the range of about 9 to about 13.5. Advantageously, the pH of the reaction system falls within the range of about 10 to about 13.

Examples of sources of silicon oxides useful in this invention include silicic acid, sodium silicate, tetraalkyl silicates and Ludox, a stabilized polymer of silicic acid manufactured by E. I. duPont de Nemours & Co. Typically, the oxide of aluminum source is sodium aluminate although equivalent species can be used such as a mixture of sodium hydroxide and aluminum sulfate.

Useful cations in this invention include alkali-metal and alkaline-earth-metal cations such as sodium, potassium, calcium and magnesium. Ammonium cations may be used in conjunction with such metal cations. Since basic conditions are required for crystallization of the molecular sieve of this invention, the source of such cation usually is a hydroxide such as sodium hydroxide.

The organic template compound useful in this invention is 2-aminopyridine. Chemically equivalent substituted 2-aminopyridines also may be used. It is believed that the spacial relationship between the basic nitrogens in 2-aminopyridine determine the placing of $AlO_4$ groups in the resulting molecular sieve possessing unique properties.

Generally, corresponding germanium compounds can be substituted for the silicon oxides and corresponding gallium compounds can be substituted for the aluminates as described herein.

In a more detailed description of a typical preparation of this invention, suitable quantities of sodium hydroxide and sodium aluminate are dissolved in distilled or deionized water followed by addition of the organic template. Preferably, the pH is adjusted between 10 and 13.5 using a compatible base or acid such as sodium bisulfate or sodium hydroxide. After sufficient quantities of silicic acid polymer (Ludox) are added with intensive mixing, preferably the pH is again checked and adjusted to a range of about 9 to about 13.5, preferably about 10 to about 13. For synthesis of active mordenite and ferrierite sieves, a pH of about 13 to 13.3 is preferred. The resulting slurry is transferred to a closed crystallization vessel and moderately stirred at a pressure at least the vapor pressure of water for a time sufficient to permit crystallization which usually is about 0.25 to about 20 days, typically is about one to about ten days and preferably is about five to about seven days, at a temperature ranging from about 100° to about 250° C., preferably about 125° to about 200° C. Preferably, the crystallization temperature is maintained below the decomposition temperature of the organic template compound. Especially preferred conditions are stirring at about 165° C. for about five to about seven days. Samples of material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically about 25°-200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, the mildly dried product is calcined at temperatures ranging from about 260° C. to about 850° C. and preferably about 525° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about four hours.

The crystalline aluminosilicates prepared according to this invention can be used as catalysts or as adsorbents whether in the alkali-metal or alkaline-earth-metal forms, the ammonium form, the hydrogen form, or any other univalent or multivalent cationic form. Mixtures of cations may be employed.

A catalytically active material can be placed onto the aluminosilicate structure by ion exchange, impregnation, a combination thereof, or other suitable contact means. Advantageously, before placing a catalytically active metal ion or compound on the aluminosilicate structure, the aluminosilicate is in the hydrogen form which, typically, is produced by exchange with ammonium ion followed by calcination.

The original cation in the crystalline aluminosilicate prepared according to this invention, which usually is sodium ion, can be replaced by ion exchange with other cations including other metal ions and their amine complexes, alkylammonium ions, ammonium ions, hydrogen ions, and mixtures thereof. Preferred replacing cations are those which render the crystalline aluminosilicate catalytically active, especially for hydrocarbon conversion. Typical catalytically active ions include hydrogen, metal ions of Groups IB, IIA, IIB, IIIA and VIII, and of manganese, vanadium, chromium, uranium, and rare earth elements.

Also water soluble salts of catalytically active materials can be impregnated onto the crystalline aluminosilicate of this invention. Such catalytically active materials include hydrogen, metals of Groups IB, IIA, IIB, IIIA, IVB, VB, VIB, VIIB and VIII, and rare earth elements. Compounds of catalytically active metal compounds such as oxides of molybdenum, chromium and tungsten can be impregnated on the crystalline aluminosilicate prepared according to this invention.

Ion exchange and impregnation techniques are well known in the art. Typically, an aqueous solution of a cation species is exchanged one or more times at about 85° to about 100° C. Impregnation of a catalytically active compound on the aluminosilicate or on a composition comprising the crystalline aluminosilicate suspended in and distributed throughout a matrix of a support material such as a porous refractory inorganic oxide such as alumina, often results in a suitable catalytic composition. A combination of ion exchange and impregnation can be used. The choice of catalytically active materials to be placed on the crystalline aluminosilicate depends on the intended process use.

The amount of catalytically active metal placed on the aluminosilicate of this invention can vary from less than one weight percent to about thirty weight percent, typically from about 0.05 to about 25 weight percent, depending on the process use intended. The optimum amount can be determined easily by routine experimentation.

If desired, a hydrogenating component, such as ions or compounds of tungsten, vanadium, molybdenum, rhenium, nickel, cobalt, chromium, manganese, a noble metal such as platinum or palladium, or a rare earth element, can be ion exchanged, impregnated or physically admixed with compositions prepared according to this invention.

The crystalline aluminosilicate prepared according to this invention may be incorporated as a pure material in a catalyst or adsorbent, or may be admixed with or incorporated within various binders or matrix materials depending upon the intended process use. The crystalline aluminosilicate can be combined with active or inactive materials, synthetic or naturally-occurring zeolites, as well as inorganic or organic materials which would be useful for binding the aluminosilicate. Well-known materials include silica, silica-alumina, alumina, alumina sols, hydrated aluminas, clays such as bentonite or kaolin, or other binders well known in the art. Typically, the aluminosilicate is incorporated within a matrix material by blending with a sol or gel of the matrix material and gelling the resulting mixture. Also, solid particles of the aluminosilicate and matrix material can be physically admixed. Typically, such aluminosilicate compositions can be pelletized or extruded into useful shapes. The crystalline aluminosilicate content can vary anywhere from a few up to 100 wt.% of the total composition. Typical catalytic compositions contain about 1 wt.% to about 100 wt.% crystalline aluminosilicate material and preferably contain about 2 wt.% to about 65 wt.% of such material.

Catalytic compositions comprising the crystalline aluminosilicate material of this invention and a suitable matrix material can be formed by adding a finely-divided crystalline aluminosilicate and a catalytically active metal compound to an aqueous sol or gel of the matrix material. The resulting mixture is thoroughly blended and gelled, typically, by adding a material such as ammonium hydroxide. The resulting gel can be dried and calcined to form a composition in which the crystalline aluminosilicate and catalytically active metal compound are distributed throughout the matrix material.

The crystalline aluminosilicates prepared according to this invention are useful as catalysts for various hydrocarbon conversion processes and are suitable for chemical adsorption. Some of the hydrocarbon conversion processes for which the aluminosilicate appear to have useful catalytic properties are fluidized catalytic cracking; hydrocracking; isomerization of normal paraffins and napthenes; reforming of naphthas and gasoline-boiling-range feedstocks; isomerization of alkylaromatics, such as xylenes; disproportionation of aromatics, such as toluene, to form mixtures of other more valuable products including benzene, xylene, and other higher methyl substituted benzenes; hydrotreating; alkylation, including (a) alkylation of benzene with ethylene, ethanol or other ethyl carbocation precursor to yield ethylbenzene, (b) alkylation of benzene or toluene with methanol or other methanol or carbocation precursor to yield xylenes, especially p-xylene, or pseudocumene, (c) alkylation of benzene with propylene and (d) alkylation of $C_3$ to $C_5$ paraffins with $C_5$ to $C_3$ olefins; hydrodealkylation; hydrodesulfurization; and hydrodenitrogenation. They are particulary suitable for the isomerization of alkylaromatics, such as xylenes, and for the conversion of ethylbenzene. Such aluminosilicates, in certain ion-exchanged forms, can be used to convert alcohols, such as methanol, to hydrocarbon products, such as aromatics or olefins, or for hydroformylation and syngas conversion.

The molecular sieve composition prepared according to this invention especially is suited for hydrodealkylation of alkyl-substituted aromatics. "Hydrodealkylation" is the process to replace an alkyl group containing two or more carbon atoms on an aromatic nucleus with hydrogen. Suitable operating conditions for hydrodealkylating a feed containing an alkyl-substituted aromatic, such as ethylbenzene, comprise a temperature of about 95° C. to about 545° C., a hydrogen-to-hydrocarbon mole ratio of about 0 to about 20, a weight hourly space velocity (WHSV) of about 0.01 weight unit of feed per hour per weight unit of catalyst (hr.$^{-1}$) to about 90 hr.$^{-1}$, and a pressure of about 0 psig to about 1,000 psig. Advantageously, the conditions comprise a temperature of about 250° C. to about 480° C., a hydrogen-to-hydrocarbon mole ratio of about 1 to about 12, a WHSV of about 1 hr.$^{-1}$ to about 20 hr.$^{-1}$, and a pressure of about 0 psig to about 500 psig. The preferred conditions for the isomerization of xylenes comprise a temperature of about 315° C. to about 455° C., a hydrogen-to-hydrocarbon mole ratio of about 2 to about 8, a WHSV of about 1 hr.$^{-1}$ to about 10 hr.$^{-1}$, and a pressure of about 0 psig to about 300 psig. The choice of catalytically active metals to be placed on the crystalline aluminosilicate can be selected from any of those well known in the art. Nickel seems to be appropriate for hydrodealkylation of aromatics.

The following Examples demonstrate but do not limit the present invention.

EXAMPLES I-III

Samples of crystalline aluminosilicate were prepared by dissolving measured quantities of sodium aluminate and sodium hydroxide in distilled water followed by a quantity of 2-aminopyridine. To this solution, Ludox HS-40 was added with vigorous stirring continuing for about 15-35 minutes after addition. The resulting curdy, gelatinous mixture was placed in a stirred, sealed crystallization vessel to crystallize at 165° C. for seven days. The resulting crystalline material was recovered by filtration, washed thoroughly with distilled water, and dried in a forced draft oven at 121° C. for 16 hours. The dried material was calcined at 1,000° F. (538° C.) for four hours. X-ray diffraction analyses of the calcined solids show patterns similar to a mordenite molecular sieve. d-Spacings for Example I are listed in Table I. Details of the preparation of Examples I-III are shown in Table II.

The X-ray powder diffraction measurements shown herein were obtained on a Phillips diffractometer using copper K alpha radiation in conjunction with an AMR focusing monochromometer and a theta angle compensating slit in which aperture varies with theta angle. Data generated by the diffractometer were processed through a Canberra hardware/software package and presented in a strip chart and in a numerical printout of relative intensity (peak height), interplaner spacing and two-theta angle. The compensating slit and the Canberra package tend to increase the peak-to-background ratios while reducing the peak intensities at low theta angles [large interplanar spacings] and increasing the peak intensities at high theta angles [small interplanar spacings].

In reporting the results obtained, relative intensities, i.e., relative peak heights, were arbitrarily assigned the following values:

| Relative Peak Height | Assigned Strength |
|---|---|
| less than 10 | VW (very weak) |
| 10–19 | W (weak) |
| 20–39 | M (medium) |
| 40–69 | MS (medium strong) |
| 70–89 | S (strong) |
| greater than 90 | VS (very strong) |

Interplanar spacings are represented by "d" and are expressed in terms of Angstrom units (Å) and nanometers (nm).

Thirty-gram portions of the sieve prepared in Examples I–III were exchanged with 60 grams of ammonium acetate in 450 milliliters of distilled water at 90° C. for 1.5 hours. The sieve was then filtered, washed with approximately 400 milliliters of distilled water, and filter dried. This procedure was repeated to obtain a total of five ammonium acetate exchanges. The washed sieve was dried at 165° C. for approximately 16 hours (overnight). The dried sieve was program calcined with a program consisting of (a) a linear temperature rise of less than or equal to 200° F. per hour from 200° F. to 900° F., (b) holding at 900° F. for 4 hours, and (c) decreasing the temperature at a maximum of 200° F. per hour from 900° F. to 200° F. per hour. Ten grams of calcined sieve then was exchanged with $Ni(NH_3)_6^{++}$ with a solution containing 100 milliliters of 5% $Ni(NO_3)_2 \cdot 6H_2O$ in distilled water to which was added approximately 20 milliliters of concentrated ammonium hydroxide. The pH of the exchange solution was 11.6. After exchanging for 1.5 hours at 90° C., the sieve was filtered from the exchange solution, washed with approximately 200 milliliters of distilled water and dried overnight in the forced draft oven at 165° C. The dried and exchanged sieve was program calcined at 900° F. with the program calcination procedure described above. The catalyst was prepared by dispersing the above calcined and exchanged sieve in PHF-alumina which is initially an acetic acid stabilized alumina hydrosol containing about 10% solids. To 10.5 grams of calcined and exchanged sieve were added about 11.0 grams of distilled water to fill the sieve pores with water. The wet sieve then was added and thoroughly mixed with 53.3 grams of alumina hydrosol. The mixture was gelled (solidified) with the addition of a solution containing 3.5 milliliters of distilled water and 3.5 milliliters of concentrated ammonium hydroxide. The resulting solid was then dried overnight in a forced air oven at 165° C. The dried solid was program calcined at 900° F. with the program as described above. The calcined solid was crushed and sized to 30 to 50 mesh (U.S. Sieve Series) and recalcined with the above 900° F. program calcination. X-ray diffraction analysis of the calcined solid yielded a pattern similiar to a mordenite-like molecular sieve as shown in Table I.

One gram of the 30–50 mesh aluminosilicate material was placed in a small screening reactor and sulfided by contacting it with $H_2S$ gas at room temperature. The sulfided catalyst was heat treated at 316° C. for one hour in hydrogen at 150 psig. A hydrocarbon feed was passed on a once-through operation over the catalyst at 150 psig. After about 138 hours on stream, feed and liquid effluents were analyzed and results calculated for catalysts made from compositions of Examples I–III are shown in Tables III–V respectively. Because of equipment limitations on the screening unit, only the liquid analysis is shown. The amount of ethylbenzene converted by hydrodeethylation were calculated based on the following assumed transalkylation pathways:

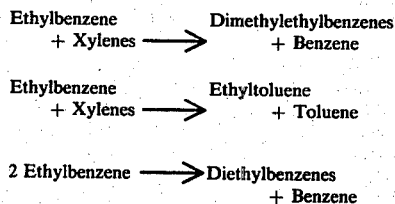

Based on these pathways the amount of ethylbenzene converted by hydrodeethylation in percent equals the moles of ethylbenzene reacted minus the sum of the moles of ethylbenzene converted by such transalkylation pathways all divided by the moles of ethylbenzene reacted and multiplied by 100. The catalyst was effective in deethylating ethylbenzene.

TABLE I

| d-spacing | | | |
|---|---|---|---|
| Å | nm | I/Io | Assigned Strength |
| 9.29 | 0.929 | 39 | M |
| 6.64 | 0.664 | 50 | MS |
| 4.57 | 0.457 | 37 | M |
| 4.03 | 0.403 | 71 | MS–S |
| 3.50 | 0.350 | 97 | VS |
| 3.41 | 0.341 | 100 | VS |
| 3.24 | 0.324 | 79 | S |
| 2.91 | 0.291 | 52 | MS |
| 2.52 | 0.252 | 31 | M |
| 2.05 | 0.205 | 26 | M |
| 1.88 | 0.188 | 31 | M |

TABLE II

| | Ex. I | Ex. II | Ex. III |
|---|---|---|---|
| Water (grams) | 600 | 600 | 600 |
| Sodium Hydroxide (grams) | 4.0 | 10.0 | 10.0 |
| Sodium aluminate (grams) | 16.0 | 20.0 | 20.0 |
| 2-Aminopyridine (grams) | 96.0 | 140 | 140 |
| Ludox HS-40 (grams) | 96.0 | 140 | 140 |
| Final pH | 13.1 | 12.9[1] | 13.3[2] |

[1] pH adjusted by addition of 30.0 grams of sodium bisulfate.
[2] pH adjusted by addition of 30.0 grams of sodium bisulfate and 1.9 grams of sodium hydroxide.

TABLE III

| | Example I |
|---|---|
| Conditions | |

TABLE III-continued

Example I

| | | | | | | | | | |
|---|---|---|---|---|---|---|---|---|---|
| Reactor Temp. (°C.) | | 317 | 317 | 337 | 359 | 383 | 404 | 427 | 449 | 406 |
| Reactor Pressure (psig) | | 150 | 150 | 150 | 150 | 150 | 150 | 150 | 150 | 150 |
| Space Velocity (WHSV, hr.$^{-1}$) | | 4.53 | 5.22 | 5.57 | 6.26 | 5.25 | 5.84 | 5.35 | 6.21 | 8.81 |
| Hydrogen/hydrocarbon (molar ratio) | | 8.4 | 7.3 | 6.8 | 6.1 | 7.2 | 6.5 | 7.1 | 6.1 | 4.3 |
| Components (wt. %) | Feed | | | | | | | | | |
| Paraffins and Naphthenes | 0.03 | 0.18 | 0.20 | 0.15 | 0.49 | 0.18 | 0.08 | 0.16 | 0.18 | 0.16 |
| Benzene | 0.00 | 1.67 | 0.58 | 0.88 | 1.40 | 2.92 | 3.67 | 7.29 | 8.08 | 3.57 |
| Toluene | 0.06 | 0.40 | 0.55 | 0.80 | 1.25 | 2.06 | 2.37 | 4.08 | 4.65 | 1.77 |
| Ethylbenzene | 19.33 | 17.55 | 18.73 | 18.25 | 17.19 | 14.94 | 13.75 | 8.12 | 7.12 | 14.16 |
| p-Xylene | 9.60 | 14.42 | 11.34 | 11.91 | 12.55 | 14.26 | 14.32 | 16.86 | 16.12 | 14.18 |
| m-Xylene | 47.47 | 42.84 | 45.52 | 44.75 | 43.95 | 42.20 | 42.40 | 40.61 | 40.33 | 42.53 |
| o-Xylene | 23.37 | 21.13 | 22.19 | 21.80 | 21.28 | 20.54 | 20.59 | 19.44 | 19.80 | 20.96 |
| Ethyltoluenes | 0.11 | 0.29 | 0.23 | 0.35 | 0.45 | 0.63 | 0.59 | 0.60 | 0.68 | 0.49 |
| Trimethylbenzenes | 0.01 | 0.47 | 0.28 | 0.41 | 0.53 | 0.93 | 1.00 | 1.58 | 1.32 | 0.67 |
| Diethylbenzenes | — | 0.30 | 0.27 | 0.41 | 0.57 | 0.83 | 0.77 | 0.65 | 0.68 | 1.05 |
| Dimethylethyl-benzenes | — | 0.24 | .010 | 0.25 | 0.36 | 0.52 | 0.48 | 0.60 | 0.54 | 0.45 |
| Results[1] | | | | | | | | | | |
| PATE - p-Xylene | | 54.4 | 20.2 | 27.4 | 35.7 | 56.5 | 56.8 | 86.7 | 80.5 | 54.6 |
| Ethylbenzene conversion (%) | | 9.2 | 3.1 | 5.6 | 11.1 | 22.7 | 28.9 | 58.0 | 63.1 | 26.7 |
| Ethylbenzene conversion by hydrodeethylation (%) | | 54 | 0 | 47 | 31 | 60 | 60 | 22 | 37 | 54 |

[1]PATE = Percent Approach to Theoretical Equilibrium

TABLE IV

Example II

| | | | | | | | | | |
|---|---|---|---|---|---|---|---|---|---|
| Conditions | | | | | | | | | | |
| Reactor Temp. (°C.) | | 316 | 316 | 338 | 361 | 382 | 404 | 426 | 449 | 405 |
| Reactor Pressure (psig) | | 150 | 150 | 150 | 150 | 150 | 150 | 150 | 150 | 150 |
| Space Velocity (WHSV, hr.$^{-1}$) | | 4.62 | 4.97 | 5.65 | 5.77 | 3.35 | 5.94 | 5.03 | 6.01 | 7.97 |
| Hydrogen/hydrocarbon (molar ratio) | | 8.2 | 7.7 | 6.7 | 6.6 | 11.4 | 6.4 | 7.6 | 6.3 | 4.8 |
| Components (wt. %) | Feed | | | | | | | | | |
| Paraffins and Naphthenes | 0.03 | 0.24 | 0.30 | 0.21 | 0.24 | 0.27 | 0.22 | 0.19 | 0.18 | 0.11 |
| Benzene | 0.00 | 0.51 | 0.47 | 0.90 | 1.56 | 3.21 | 3.82 | 5.77 | 6.60 | 3.30 |
| Toluene | 0.06 | 0.39 | 0.35 | 0.53 | 0.83 | 1.61 | 1.99 | 3.30 | 3.68 | 1.53 |
| Ethylbenzene | 19.33 | 18.86 | 18.81 | 18.55 | 17.45 | 14.79 | 13.86 | 11.00 | 10.10 | 14.90 |
| p-Xylene | 9.60 | 10.48 | 10.33 | 10.80 | 11.16 | 12.59 | 12.85 | 14.00 | 13.88 | 12.28 |
| m-Xylene | 47.47 | 46.38 | 46.62 | 45.79 | 45.60 | 44.43 | 44.04 | 42.69 | 42.33 | 44.51 |
| o-Xylene | 23.37 | 22.65 | 22.64 | 22.54 | 22.30 | 21.84 | 21.62 | 20.93 | 20.99 | 21.92 |
| Ethyltoluenes | 0.11 | 0.16 | 0.18 | 0.23 | 0.26 | 0.15 | 0.38 | 0.46 | 0.47 | 0.32 |
| Trimethylbenzenes | 0.01 | 0.09 | 0.08 | 0.12 | 0.20 | 0.45 | 0.53 | 0.80 | 0.78 | 0.36 |
| Diethylbenzenes | — | 0.21 | 0.20 | 0.29 | 0.34 | 0.44 | 0.49 | 0.54 | 0.62 | 0.60 |
| Dimethylethyl-benzenes | — | 0.02 | 0.02 | 0.04 | 0.06 | 0.22 | 0.20 | 0.32 | 0.38 | 0.17 |
| Results[1] | | | | | | | | | | |
| PATE - p-Xylene | | 10.4 | 8.7 | 14.4 | 18.5 | 34.5 | 38.2 | 53.0 | 52.8 | 31.6 |
| Ethylbenzene conversion (%) | | 2.4 | 2.7 | 4.0 | 9.7 | 23.5 | 28.3 | 43.1 | 47.7 | 22.9 |
| Ethylbenzene conversion by hydrodeethylation (%) | | 17 | 24 | 20 | 62 | 80 | 79 | 83 | 83 | 71 |

[1]PATE = Percent Approach to Theoretical Equilibrium

TABLE V

Example III

| | | | | | | | | | |
|---|---|---|---|---|---|---|---|---|---|
| Conditions | | | | | | | | | |
| Reactor Temp. (°C.) | 316 | 316 | 338 | 360 | 382 | 404 | 425 | 449 | 471 |
| Reactor Pressure (psig) | 150 | 150 | 150 | 150 | 150 | 150 | 150 | 150 | 150 |
| Space Velocity | | | | | | | | | |

TABLE V-continued

Example III

| (WHSV, hr.$^{-1}$) | | 2.20 | 3.02 | 6.66 | 6.73 | 6.64 | 7.07 | 5.42 | 6.34 | 7.30 |
|---|---|---|---|---|---|---|---|---|---|---|
| Hydrogen/hydrocarbon (molar ratio) | | 17.3 | 12.6 | 5.7 | 5.7 | 5.7 | 5.4 | 7.0 | 6.0 | 5.2 |
| Components (wt. %) | Feed | | | | | | | | | |
| Paraffins and Naphthenes | 0.03 | 0.70 | — | 0.24 | 0.23 | 0.17 | 0.41 | 0.29 | 0.28 | 0.19 |
| Benzene | 0.00 | 1.28 | 1.26 | 1.39 | 2.46 | 4.16 | 6.01 | 8.39 | 9.49 | 9.45 |
| Toluene | 0.06 | 1.77 | 1.05 | 0.99 | 1.56 | 2.47 | 3.57 | 5.73 | 6.89 | 7.63 |
| Ethylbenzene | 19.33 | 17.02 | 17.17 | 17.26 | 15.59 | 12.75 | 9.77 | 6.33 | 4.66 | 4.06 |
| p-Xylene | 9.60 | 14.57 | 13.16 | 12.65 | 13.60 | 14.95 | 15.90 | 16.81 | 16.91 | 16.66 |
| m-Xylene | 47.47 | 41.48 | 43.69 | 44.22 | 43.24 | 42.24 | 40.83 | 39.27 | 38.60 | 38.86 |
| o-Xylene | 23.37 | 20.51 | 21.43 | 21.66 | 21.17 | 20.67 | 19.98 | 19.14 | 19.25 | 19.30 |
| Ethyltoluenes | 0.11 | 0.74 | 0.43 | 0.39 | 0.49 | 0.29 | 0.74 | 0.82 | 0.73 | 0.67 |
| Trimethylbenzenes | 0.01 | 1.21 | 0.40 | 0.36 | 0.51 | 0.88 | 1.24 | 1.79 | 1.80 | 1.92 |
| Diethylbenzenes | — | 0.32 | 0.64 | 0.61 | 0.76 | 1.07 | 1.00 | 0.80 | 0.65 | 0.50 |
| Dimethylethyl- benzenes | — | 0.36 | 0.19 | — | 0.39 | 0.31 | 0.53 | 0.62 | 0.73 | 0.73 |
| Results[1] | | | | | | | | | | |
| PATE - p-Xylene | | 59.7 | 41.0 | 35.3 | 46.8 | 62.3 | 75.9 | 90.4 | 93.5 | 91.1 |
| Ethylbenzene conversion (%) | | 11.9 | 11.2 | 10.7 | 19.3 | 34.0 | 49.5 | 67.2 | 75.9 | 79.0 |
| Ethylbenzene conversion by hydrodeethylation (%) | | 42 | 33 | 41 | 51 | 68 | 73 | 82 | 85 | 88 |

[1]PATE = Percent Approach to Theoretical Equilibrium

COMPARATIVE RUN A

A crystalline aluminosilicate was prepared in a manner similar to that described in Examples I–III except that triethanolamine was used as a template compound in place of 2-aminopyridine. Details of the preparation of Run A are shown in Table VI. The resulting solid material was subjected to X-ray diffraction analysis which showed a pattern similar to a mordenite molecular sieve. A catalyst was prepared and tested as described in Examples I–III and the results therefrom are shown in Table VII.

TABLE VI

| | Run A |
|---|---|
| Water (grams) | 1,200 |
| Sodium Hydroxide (grams) | 10 |
| Sodium Aluminate (grams) | 20 |
| Triethanolamine (grams) | 240 |
| Ludox HS-40 (grams) | 240 |

TABLE VII

Run A

| Conditions | | | | | | | | | | |
|---|---|---|---|---|---|---|---|---|---|---|
| Reactor Temp. (°C.) | | 316 | 316 | 316 | 327 | 338 | 360 | 349 | 338 | 327 |
| Reactor Pressure (psig) | | 150 | 150 | 150 | 150 | 150 | 150 | 150 | 150 | 150 |
| Space Velocity (WHSV, hr.$^{-1}$) | | 2.55 | 1.55 | 3.51 | 3.96 | 3.61 | 5.77 | 5.01 | 4.88 | 4.62 |
| Hydrogen/hydrocarbon (molar ratio) | | 14.9 | 24.5 | 10.8 | 9.6 | 10.5 | 6.6 | 7.6 | 7.8 | 8.2 |
| Components (wt. %) | Feed | | | | | | | | | |
| Paraffins and Naphthenes | 0.03 | 0.76 | 0.84 | 0.57 | 0.50 | 0.23 | 0.34 | 0.36 | 0.29 | 0.24 |
| Benzene | — | 0.90 | 0.82 | 0.72 | 0.77 | 1.07 | 1.45 | 1.31 | 1.06 | 0.78 |
| Toluene | 0.06 | 1.96 | 1.09 | 0.89 | 1.03 | 1.52 | 2.22 | 1.91 | 1.44 | 0.94 |
| Ethylbenzene | 19.33 | 16.68 | 18.06 | 18.38 | 17.77 | 17.77 | 17.03 | 16.96 | 17.58 | 18.19 |
| p-Xylene | 9.61 | 14.04 | 14.25 | 14.09 | 14.90 | 15.85 | 16.67 | 16.31 | 15.80 | 14.83 |
| m-Xylene | 47.47 | 41.90 | 43.24 | 43.83 | 43.61 | 41.97 | 41.23 | 41.34 | 42.19 | 43.49 |
| o-Xylene | 23.37 | 19.46 | 19.49 | 19.82 | 19.27 | 18.52 | 18.19 | 18.13 | 18.67 | 19.49 |
| Ethyltoluenes | | 0.11 | 0.93 | 0.42 | 0.34 | 0.41 | 0.74 | 0.66 | 0.53 | 0.38 |
| Trimethylbenzenes | | 0.01 | 1.88 | 0.87 | 0.71 | 0.84 | 0.45 | 1.51 | 1.16 | 0.76 |
| Diethylbenzenes | | — | 0.63 | 0.37 | 0.23 | 0.36 | 0.66 | 0.62 | 0.50 | 0.37 |
| Dimethylethyl- benzenes | | — | 0.76 | 0.52 | 0.41 | 0.53 | 0.97 | 0.93 | 0.74 | 0.52 |
| Results[1] | | | | | | | | | | |
| PATE - p-Xylene | | 55.4 | 54.5 | 51.2 | 61.0 | 74.3 | 84.7 | 81.1 | 73.0 | 54.4 |
| Ethylbenzene conversion (%) | | 16.3 | 9.4 | 7.8 | 8.1 | 10.5 | 14.6 | 14.9 | 11.8 | 8.7 |
| Ethylbenzene conversion by hydrodeethylation (%) | | 12 | 39 | 6 | 20 | 0 | 0 | 7 | 0 | 0 |

[1]Percent Approach to Theoretical Equilibrium

EXAMPLE IV

A crystalline aluminosilicate was prepared in a manner similar to that described in Examples I–III except that a relatively lower amount of sodium aluminate was used. Details of the preparation of Example IV are shown in Table VIII. The resulting solid material was subjected to X-ray diffraction analysis which showed a pattern listed in Table IX identified as ZSM-5 like.

A catalyst was prepared and tested as described in Examples I–III and the results therefrom are shown in Table X.

TABLE VIII

|  | Ex. IV[(1)] | Ex. V[(1)] | Ex. VI[(1) (2)] |
|---|---|---|---|
| Water (grams) | 300 | 600 | 450 |
| Sodium Hydroxide (grams) | 2.5 | 16.0 | 1.35 |
| Sodium Aluminate (grams) | 2.4 | 10.0 | 6.75 |
| 2-Aminopyridine (grams) | 57.0 | 150 | 167 |
| Ludox HS-40 (grams) | 57.0 | 125 | 240 |
| Final pH | — | — | 11.4 |

[(1)]Washed material after crystallization was dried overnight at 165° C.
[(2)]Crystallized for 28 days.

TABLE IX

| d-spacing Å | nm | I/Io | Assigned Strength |
|---|---|---|---|
| 11.18 | 1.118 | 67 | MS |
| 10.04 | 1.004 | 48 | MS |
| 9.02 | 0.902 | 20 | M |
| 7.37 | 0.737 | 6 | VW |
| 7.08 | 0.708 | 5 | VW |
| 6.91 | 0.691 | 6 | VW |
| 6.70 | 0.670 | 14 | W |
| 6.51 | 0.651 | 20 | M |
| 6.32 | 0.632 | 20 | M |
| 5.98 | 0.598 | 20 | M |
| 5.71 | 0.571 | 15 | W |
| 5.57 | 0.557 | 16 | W |
| 5.40 | 0.540 | 6 | VW |
| 4.98 | 0.498 | 11 | W |
| 4.62 | 0.462 | 10 | W |
| 4.52 | 0.452 | 14 | W |
| 4.35 | 0.435 | 15 | W |
| 4.27 | 0.427 | 30 | M |
| 4.07 | 0.407 | 35 | M |
| 3.98 | 0.398 | 37 | M |
| 3.83 | 0.383 | 100 | VS |
| 3.72 | 0.372 | 64 | MS |
| 3.64 | 0.364 | 37 | M |
| 3.46 | 0.346 | 41 | MS |
| 3.35 | 0.335 | 43 | MS |
| 3.21 | 0.321 | 23 | M |
| 3.14 | 0.314 | 10 | W |
| 3.06 | 0.306 | 16 | W |
| 2.98 | 0.298 | 21 | M |
| 2.94 | 0.294 | 12 | W |
| 2.88 | 0.288 | 12 | W |
| 2.73 | 0.273 | 6 | VW |
| 2.66 | 0.266 | 3 | VW |
| 2.60 | 0.260 | 7 | VW |
| 2.58 | 0.258 | 5 | VW |
| 2.54 | 0.254 | 5 | VW |
| 2.51 | 0.251 | 11 | W |
| 2.49 | 0.249 | 14 | W |
| 2.45 | 0.245 | 7 | VW |
| 2.41 | 0.241 | 6 | VW |
| 2.39 | 0.239 | 7 | VW |
| 2.27 | 0.227 | 3 | VW |
| 2.13 | 0.213 | 3 | VW |
| 2.04 | 0.204 | 4 | VW |
| 2.00 | 0.200 | 13 | W |
| 1.99 | 0.199 | 15 | W |
| 1.95 | 0.195 | 6 | VW |

TABLE X

|  | Example IV | | | | |
|---|---|---|---|---|---|
| Conditions | | | | | |
| Reactor Temp. (°C.) | 360 | 381 | 393 | 404 | 426 |
| Reactor Pressure (psig) | 150 | 150 | 150 | 150 | 150 |
| Space Velocity (WHSV, hr.$^{-1}$) | 6.39 | 5.27 | 5.33 | 5.41 | 5.87 |
| Hydrogen/hydrocarbon (molar ratio) | 7.1 | 7.3 | 7.2 | 7.1 | 6.5 |
| Components (wt. %) | Feed | | | | | |

| Components (wt. %) | Feed | | | | | |
|---|---|---|---|---|---|---|
| Paraffins and Naphthenes | — | 0.12 | 0.09 | 0.05 | 0.07 | 0.07 |
| Benzene | — | 5.66 | 7.63 | 8.18 | 9.27 | 9.79 |
| Toluene | 0.07 | 3.85 | 5.97 | 7.69 | 8.62 | 12.04 |
| Ethylbenzene | 18.40 | 8.81 | 5.66 | 4.23 | 2.88 | 1.88 |
| p-Xylene | 10.10 | 16.01 | 16.66 | 16.90 | 16.80 | 16.37 |
| m-Xylene | 46.84 | 42.52 | 41.46 | 40.73 | 39.92 | 38.39 |
| o-Xylene | 24.06 | 20.02 | 19.26 | 18.80 | 19.02 | 18.36 |
| Ethyltoluenes | — | 0.94 | 1.03 | 1.05 | 0.86 |
| Trimethylbenzenes | 0.53 | 0.47 | 0.79 | 1.00 | 1.18 |
| Diethylbenzenes | — | 1.11 | 0.68 | 0.49 | 0.29 |
| Dimethylethylbenzenes | — | 0.45 | 0.65 | 0.73 | 0.63 |
| Results[(1)] | | | | | |
| PATE - p-Xylene | | 73.6 | 83.3 | 88.3 | 91.0 | 92.8 |
| Ethylbenzene conversion (%) | | 52.1 | 69.2 | 77.0 | 85.3 | 90.4 |
| Ethylbenzene conversion by hydrodeethylation (%) | | 69 | 80 | 84 | 89 | 91 |

[(1)]PATE = Percent Approach to Theoretical Equilibrium

EXAMPLE V

A crystalline aluminosilicate was prepared in a manner similar to that described in Examples I–III except that a relatively lower amount of sodium aluminate was used. Details of the preparation of Example V are shown in Table VIII. The resulting solid material was subjected to X-ray diffraction analysis which showed a pattern listed in Table XI identified as ferrierite-like.

TABLE XI

| d-spacing Å | nm | I/Io | Assigned Strength |
|---|---|---|---|
| 9.61 | 0.961 | 43 | MS |
| 7.09 | 0.709 | 21 | M |
| 6.64 | 0.664 | 33 | M |
| 5.61 | 0.561 | 36 | M |
| 4.00 | 0.400 | 73 | S |
| 3.86 | 0.386 | 53 | MS |
| 3.78 | 0.378 | 53 | MS |
| 3.67 | 0.367 | 39 | M |
| 3.54 | 0.354 | 66 | S |
| 3.48 | 0.348 | 100 | VS |
| 3.39 | 0.339 | 77 | S |
| 3.23 | 0.323 | 62 | MS |
| 3.15 | 0.315 | 37 | M |
| 2.90 | 0.290 | 40 | M-MS |
| 3.06 | 0.306 | 29 | M |
| 2.00 | 0.200 | 28 | M |
| 1.92 | 0.192 | 27 | M |

EXAMPLE VI

A crystalline aluminosilicate was prepared in a manner similar to that described in Example V. Details of the preparation of Example VI are shown in Table VIII. The resulting solid material was identified as ferrierite-like by X-ray diffraction analysis. A catalyst was prepared and tested in a manner similar to that described in Examples I–III and the results therefrom are shown in Table XII.

TABLE XII

|  | Example VI | | | |
|---|---|---|---|---|
| Conditions | | | | |
| Reactor Temp. (°C.) |  | 382 | 427 | 449 |
| Reactor Pressure (psig) |  | 150 | 150 | 150 |
| Space Velocity (WHSV, hr.$^{-1}$) |  | 6.38 | 5.80 | 5.50 |
| Hydrogen/hydrocarbon (molar ratio) |  | 5.91 | 6.50 | 6.85 |
| Components (wt. %) | Feed | | | |
| Paraffins and Naphthenes | 0.03 | 0.02 | 0.02 | 0.03 |
| Benzene | 0.06 | 0.38 | 0.51 | 1.45 |
| Toluene | 0.10 | 0.15 | 0.17 | 0.27 |
| Ethylbenzene | 17.56 | 16.94 | 16.62 | 15.30 |
| p-Xylene | 11.12 | 11.75 | 11.74 | 12.11 |
| m-Xylene | 51.09 | 50.41 | 50.54 | 50.32 |
| o-Xylene | 19.95 | 20.14 | 20.15 | 20.23 |
| Ethyltoluenes | 0.01 | 0.09 | 0.11 | 0.10 |
| Trimethylbenzenes | — | — | — | — |
| Diethylbenzenes | — | 0.12 | 0.14 | 0.20 |
| Dimethylethylbenzenes | — | — | — | — |
| Results[1] | | | | |
| PATE - p-Xylene |  | 7.4 | 7.2 | 11.4 |
| Ethylbenzene conversion (%) |  | 3.5 | 5.4 | 12.9 |
| Ethylbenzene conversion by hydrodeethylation (%) |  | 68 | 75 | 86 |

[1] PATE = Percent Approach to Theoretical Equilibrium

The data in Examples I–VI demonstrate that catalysts prepared using the crystalline aluminosilicates of this invention generally are selective in dealkylating ethylbenzene.

What is claimed is:

1. A method to prepare a crystalline aluminosilicate molecular sieve comprising (1) forming an aqueous mixture of an oxide of aluminum, an oxide of silicon, a cation and 2-aminopyridine as an organic template compound, (2) maintaining the pH of such mixture between about 9 and about 13.5 and (3) crystallizing such mixture.

2. The method of claim 1 wherein source of the oxide of aluminum is sodium aluminate.

3. The method of claim 1 wherein the composition of the mixture of initial reactants in terms of mole ratios of oxides is:

| $SiO_2/Al_2O_3$ | 2–500 |
|---|---|
| $R_2O+/[R_2O+ + M_{2/n}O]$ | 0.1–1.0 |
| $OH-/SiO_2$ | 0.005–10 |
| $H_2O/OH-$ | 10–4000 | where R is derived from 2-aminopyridine and M is at least one cation having a valence n.

4. The method of claim 1 wherein the composition of the mixture of initial reactants in terms of mole ratios of oxides is:

| $SiO_2/Al_2O_3$ | 4–20 |
|---|---|
| $R_2O+/[R_2O+ + M_{2/n}O]$ | 0.1–1.0 |
| $OH-/SiO_2$ | 0.005–10 |
| $H_2O/OH-$ | 10–4000 | where R is derived from 2-aminopyridine and M is at least one cation having a valence n.

5. The method of claim 1 wherein the composition of the mixture of initial reactants in terms of mole ratios of oxides is:

| $SiO_2/Al_2O_3$ | 8–40 |
|---|---|
| $R_2O+/[R_2O+ + M_{2/n}O]$ | 0.1–1.0 |
| $OH-/SiO_2$ | 0.005–10 |
| $H_2O/OH-$ | 10–4000 | where R is derived from 2-aminopyridine and M is at least one cation having a valence n.

6. The method of claim 3 wherein the crystalline aluminosilicate is mordenite-like.

7. The method of claim 3 wherein the crystalline aluminosilicate is ferrierite-like.

8. The method of claim 4 wherein the crystalline aluminosilicate is mordenite-like.

9. The method of claim 5 wherein the crystalline aluminosilicate is ferrierite-like.

10. The method of claim 4 wherein the silica/alumina molar ratio of initial reactants is about 8.

11. The method of claim 5 wherein the silica/alumina molar ratio of initial reactants is about 16.

12. The method of claim 1 wherein the pH of the mixture is maintained between about 10 and about 13.

13. The method of claim 1 wherein the crystallizing mixture is maintained at about 100° C. to about 250° C. for about 0.25 to about 20 days.

14. The method of claim 1 wherein the crystallizing mixture is maintained at about 125° C. to about 200° C. for about one to about seven days.

15. The method of claim 3 wherein M is an alkali metal or alkaline earth metal cation.

16. The method of claim 1 wherein the oxide of silicon source is a silicic acid polymer.

17. The method of claim 1 wherein a catalytically active material is placed onto the crystalline aluminosilicate.

18. The method of claim 17 wherein the catalytically active ion is ion exchanged onto the crystalline aluminosilicate.

19. The method of claim 18 wherein the catalytically active ion is hydrogen, metal ions of Groups IB, IIB, IIIA or VIII or of manganese, vanadium, chromium, uranium or rare earth elements.

20. The method of claim 19 wherein the ion is nickel ion.

21. The method of claim 1 wherein a catalytically active compound is impregnated onto the crystalline aluminosilicate.

22. The method of claim 21 wherein the catalytically active compound is a water soluble salt of hydrogen, metals of Groups IB, IIB, IIIA, IVB, VB, VIB, VIIB, or VIII, or rare earth elements.

23. The method of claim 22 wherein the catalytically active compound is a compound of molybdenum.

24. The method of claim 1 wherein the prepared molecular sieve is incorporated within a suitable matrix material.

25. The method of claim 24 wherein the matrix material is silica, silica-alumina or alumina.

* * * * *